(12) United States Patent
Kim et al.

(10) Patent No.: US 6,737,049 B1
(45) Date of Patent: May 18, 2004

(54) CATIONIC POLYMERS AND THEIR USE

(75) Inventors: Son Nguyen Kim, Hemsbach (DE); Axel Sanner, Frankenthal (DE); Volker Schehlmann, Schifferstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/762,039

(22) PCT Filed: Aug. 19, 1999

(86) PCT No.: PCT/EP99/06059

§ 371 (c)(1), (2), (4) Date: Feb. 1, 2001

(87) PCT Pub. No.: WO00/11051

PCT Pub. Date: Mar. 2, 2000

(30) Foreign Application Priority Data

Aug. 24, 1998 (DE) .......................... 198 38 196

(51) Int. Cl.$^7$ ................................. A61K 7/06
(52) U.S. Cl. ......................................... 424/70.1
(58) Field of Search ........................ 424/70.1

(56) References Cited

U.S. PATENT DOCUMENTS

| | | | |
|---|---|---|---|
| 5,132,417 A | * | 7/1992 | Potthoff-Karl et al. ...... 526/264 |
| 5,972,356 A | * | 10/1999 | Peffly et al. ................. 424/401 |

FOREIGN PATENT DOCUMENTS

| | | |
|---|---|---|
| EP | 100 890 | 2/1984 |
| EP | 0 100 890 | * 2/1984 |
| EP | 373 442 | 6/1990 |
| WO | WO 96/19966 | 7/1996 |

OTHER PUBLICATIONS

WPI, Derwent accession No. 1984–024545, abstract (EP 100890).*
DWPI, Derwent accession No. 1984–024545, abstract (EP 100890).*
WPI, Derwent accession No. 1984–024545, abstract (EP 0 100 890).*

* cited by examiner

Primary Examiner—Thurman K. Page
Assistant Examiner—Blessing Fubara
(74) Attorney, Agent, or Firm—Keil & Weinkauf

(57) ABSTRACT

Cationic polymers are obtainable by free-radical copolymerization, of a) from 50 to 70% by weight of one or more monomers of the formula I

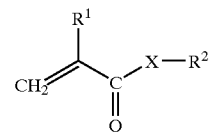

(I)

$X=O, NR^1$,
$R^1=H, C_1–C_8$-alkyl,
$R^2$=tert-butyl, (b) from 5 to 45% by weight of one or more monomers of the formula II

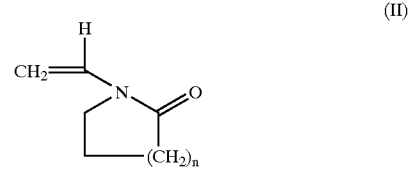

(II)

where n=1 to 3, (c) from 5 to 40% by weight of a monoethylenically unsaturated monomer having at least one amine-containing group, (d) from 0 to 5% by weight of a polyalkylene oxide-containing silicone derivative, where up to 40% by weight, based on (a), (b), (c) and (d), of the monomer (a) can be replaced by a monomer of the formula I where $R^2=C_2–C_{22}$-alkyl.

6 Claims, No Drawings

CATIONIC POLYMERS AND THEIR USE

The present invention relates to cationic polymers obtainable by free-radical copolymerization of (a) from 50 to 70% by weight of one or more monomers of the formula I

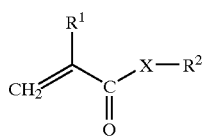

$X=O, NR^1$,
$R^1=H, C_1-C_9$-alkyl,
$R^2$=tert-butyl, (b) from 5 to 45% by weight of one or more monomers of the formula II

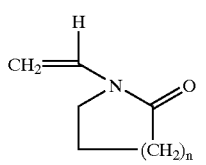

where n=1 to 3, (c) from 5 to 40% by weight of a monoethylenically unsaturated monomer having at least one amine-containing group, (d) from 0 to 5% by weight of a polyalkylene oxide-containing silicone derivative, where up to 40% by weight, based on (a), (b), (c) and (d), of the monomer (a) can be replaced by a monomer of the formula I where $R^2=C_2-C_{22}$-alkyl.

In cosmetics, polymers with film-forming properties are used for setting hair, improving its structure and for styling the hair. These hair treatment compositions generally comprise a solution of the film former in an alcohol or a mixture of alcohol and water.

Hair-setting compositions are generally sprayed onto the hair in the form of aqueous-alcoholic solutions. After the solvent has evaporated, the hair is held in the desired shape at the mutual points of contact by the polymer which is left behind. The polymers should on the one hand be sufficiently hydrophilic that they can be washed out of the hair, but on the other hand should be hydrophobic so that the hair treated with the polymers retains its shape and does not become sticky, even at high atmospheric humidity. In order to achieve an as efficient a hair-setting action as possible, it is also desirable to use polymers which have a relatively high molecular weight and a relatively high glass transition temperature (at least 15° C.).

A further requirement of hair treatment compositions is to give the hair a natural appearance and shine, e.g. even when the hair concerned is by its very nature thick and/or dark.

A disadvantage of many known hair-setting polymers is the "flaking" effect, i.e. a white, dandruff-like residue remains on the hair after combing. This is generally regarded as extremely unpleasant by the users. The "flaking" effect is particularly noticeable in people with dark hair and/or particularly thick hair. The possibility of using hair-setting formulations which have this effect is thus significantly impaired particularly in the Asian market. Possible causes of the "flaking" effect are considered to be inter alia the chemical structure of the hair-setting polymers used and, in particular, the particle size of the spray.

In addition to the abovementioned properties, hair-setting polymers should therefore preferably have high propellant compatibility in order to permit formulation in spray cans under very high pressure. This applies both to the classical propellant based on propane/butane and also to their replacements, e.g. those based on dimethyl ether.

Cationic hair-setting polymers are known, for example, from U.S. Pat. Nos. 3,914,403 and 3,954,960 and U.S. Pat. No. 4,057,533.

These polymers consist of vinylpyrrolidone, a quaternizable monomer, for example dimethylaminoethyl methacrylate (DMAEMA) and optionally a further monomer.

WO 90/01920, WO 96/19966 and WO 96/20694 describe polymers of vinylpyrrolidone, a quaternizable monomer and up to 49% of a further hydrophobic polymer.

The compatibility of these polymers with the propellant propane/butane is not, however, sufficient for all desired applications. In addition, the products are very sticky as a result of the high VP content and under conditions of high atmospheric humidity lose their setting action.

Anionic polymers with propane/butane compatibility are already known, including polymers based on tert-butyl acrylate and tert-butyl methacrylate.

EP-A-379 082 describes, for example, a hair-setting composition comprising, as film former, a copolymer which comprises, in copolymerized form, A) from 75 to 99% by weight of tert-butyl (meth)acrylate, B) from 1 to 25% by weight of (meth)acrylic acid and C) from 0 to 10% by weight of a further free-radical copolymerizable hydrophobic monomer.

Hair-setting compositions based on this copolymer which comprise only components A) and B) make the hair too hard and have too low a propane/butane compatibility. Copolymers which additionally comprise a monomer C) are in need of improvement as regards their wash-off.

DE-A-43 14 305 describes, like EP-A-379 082, a hair-setting polymer based on tert-butyl (meth)acrylate and (meth)acrylic acid which comprises from 0 to 60% by weight of a $C_1-C_{18}$-alkyl (meth)-acrylate or a mixture thereof with $N-C_1-$ to $C_{18}$-alkyl (meth)-acrylamides in copolymerized form. Although in some cases additional monomers with a carbon number greater than 8 lead to better propane/butane compatibility, the wash-off is at the same time significantly impaired.

It is an object of the present invention to provide novel cosmetic compositions, in particular hair treatment compositions, which, in addition to the good setting properties, have high propellant compatibility and essentially do not exhibit a "flaking" effect. These compositions should preferably make the hair smooth and soft.

Surprisingly, we have found that this object is achieved by cosmetic compositions which comprise at least one water-soluble or water-dispersible cationic polymer which is obtainable by free-radical polymerization of (a) from 50 to 70% by weight of one or more monomers of the formula I

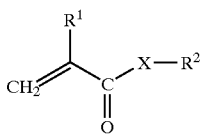

X=O, NR¹,
R1=H, $C_1$–$C_8$-alkyl,
R²=tert-butyl, (b) from 5 to 45% by weight of one or more monomers of the formula II

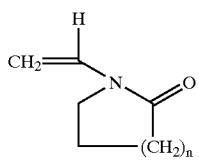

where n=1 to 3, (c) from 5 to 40% by weight of a monoethylenically unsaturated monomer having at least one amine-containing group, (d) from 0 to 5% by weight of a polyalkylene oxide-containing silicone derivative, where up to 40% by weight, based on (a), (b), (c) and (d), of the monomer (a) can be replaced by a monomer of the formula I where R²=$C_2$–$C_{22}$-alkyl.

Preferred monomers (a) are compounds of the formula I in which R1 is H and $CH_3$, and X is O and NH; particular preference is given to tert-butyl acrylate, N-tert-butylacrylamide and/or tert-butyl methacrylate.

Monomer I can also consist of mixtures having varying meanings of R1 and X, preference being given to the monomers (a) where X=NR¹ only being used in amounts up to 20% by weight, based on (a), (b) and (c).

The monomer (a) is preferably used in amounts of from 51 to 65% by weight, monomer (b) is preferably used in amounts of from 7 to 39% by weight, and monomer (c) is preferably used in amounts of from 10 to 30% by weight.

For the purposes of the present invention, the term "$C_2$–$C_{22}$-alkyl" includes straight-chain, branched and cyclic alkyl groups. They are preferably straight-chain alkyl groups and particularly preferably branched alkyl groups.

Preferred monomers of the formula I where R²=$C_2$–$C_{22}$-alkyl are the following compounds:

n-butyl (meth)acrylate, n-octyl (meth)acrylate, 1,1,3,3-tetramethylbutyl (meth)acrylate, ethylhexyl (meth)acrylate, n-nonyl (meth)acrylate, n-decyl (meth)acrylate, n-undecyl (meth)acrylate, tridecyl (meth)acrylate, myristyl (meth)acrylate, pentadecyl (meth)acrylate, pamityl (meth)acrylate, heptadecyl (meth)acrylate, nonadecyl (meth)acrylate, arrachinyl (meth)acrylate, behenyl (meth)acrylate, lignocerenyl (meth)acrylate, cerotinyl (meth)acrylate, melissinyl (meth)acrylate, palmitoeinyl (meth)acrylate, oleyl (meth)acrylate, linolyl (meth)acrylate, stearyl (meth)acrylate, lauryl (meth)acrylate and mixtures thereof and N-tert-butyl(meth)-acrylamide, N-octyl(meth)acrylamide, 1,1,3,3-tetramethylbutyl-(meth)acrylamide, ethylhexyl (meth)acrylamide, N-nonyl(meth)-acrylamide, N-decyl (meth)acrylamide, N-undecyl(meth)acrylamide, tridecyl(meth)acrylamide, myristyl(meth)acrylamide, pentadecyl(meth)acrylamide, palmityl(meth)acrylamide, heptadecyl(meth)-acrylamide, nonadecyl (meth)acrylamide, arrachinyl(meth)-acrylamide, behenyl(meth)acrylamide, lignocerenyl(meth)-acrylamide, cerotinyl(meth)acrylamide, melissinyl (meth)-acrylamide, palmitoleinyl(meth)acrylamide, oleyl(meth)acrylamide, linolyl(meth)acrylamide, stearyl(meth)acrylamide, lauryl(meth)-acrylamide and mixtures thereof.

Very particular preference is given to:

n-butyl (meth)acrylate, N-octyl(meth)acrylamide, lauryl (meth)acrylate and stearyl (meth)acrylate, where the term "(meth)acrylate" covers methacrylates and acrylates.

Monomers (b) are compounds of the structure II

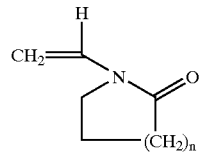

where n=1 to 3, preferably vinylpyrrolidone (VP), vinylcaprolactam (VCap) or mixtures thereof.

Some of (II), up to 4% by weight, based on the total (a)+(b)+(c), can be replaced by a hydrophilic nonionic monomer of the structure III

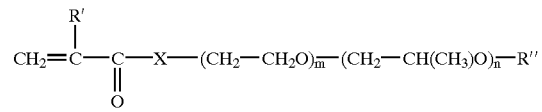

R'=H, $CH_3$

X=O, NH m=from 0 to 50 n=from 0 to 50 m+n≧5

R''=H, $C_1$–$C_{22}$-alkyl or phenyl.

In formula III, R'' is preferably a hydrogen atom and a $C_{1-4}$-alkyl group, a methyl group being particularly preferred. Examples of such a (meth)acrylate monomer include hydroxy[lacunal] (meth)-acrylate, hydroxypropyl (meth)acrylate, polyethylene glycol mono(meth)acrylate, polypropylene glycol mono(meth)acrylate, methoxypolyethylene glycol (meth)acrylate, methoxypolypropylene glycol mono (meth)acrylate, ethoxypolyethylene glycol mono(meth)-acrylate, butoxypolyethylene glycol mono(meth)acrylate and phenoxypolyethylene glycol mono(meth)acrylate.

Monomers which are used as monomers (c) are those which have at least one mononethylenically unsaturated group and at least one amine-containing group.

Preferred monomers (c) are compounds represented by the following structure IV

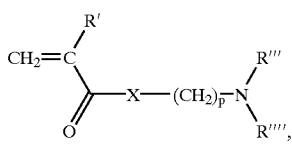

(IV)

where
R'=H, CH₃
X=O, NH
R''', R''''=are identical or different and can be CH₃, C₂H₅, C₃H₇, C₄H₉, tert-C₄H₉
p=1 to 5
Particularly suitable monomers (c) are:
N,N-dimethylaminoethyl (meth)acrylate
N,N-dimethylaminopropyl (meth)acrylate
N,N-dimethylaminoethyl(meth)acrylamide
N,N-dimethylaminopropyl(meth)acrylamide.
Very particularly suitable monomers (c) are:
N,N-dimethylaminoethyl methacrylate
N,N-dimethylaminoethylmethacrylamide
N,N-dimethylaminopropylmethacrylamide.

The monomers (c) are used in amounts of from 5 to 40% by weight, preferably from 10 to 30% by weight.

Suitable silicone derivatives (d) are the compounds known under the INCI name dimethicone copolyols or silicone surfactants, such as, for example, those obtainable under the trade names Abil® (T. Goldschmidt), Alkasil® (Rhône-Poulenc), Silicone Polyol Copolymer® (Genesee), Belsil® (Wacker), Silwet® (Witco, Greenwich, Conn., USA) or Dow Corning (Dow Corning). These include compounds with the CAS numbers 64365-23-7; 68937-54-2; 68938-54-5; 68937-55-3.

The monomers of the groups (a) to (d) can in each case be used individually or in a mixture with other monomers from the same group.

The polymers can be prepared by processes of free-radical initiated polymerization known per se, e.g. by solution polymerization, emulsion polymerization, suspension polymerization, precipitation polymerization, inverse suspension polymerization or inverse emulsion polymerization, without limiting the methods which can be used thereto.

The polymers are advantageously prepared using solution polymerization in solvents such as water, methanol, ethanol, isopropanol or mixtures of these solvents. The amounts of monomers and solvents are expediently chosen to give from 30 to 70% by weight strength solutions.

The polymerization is usually carried out at temperatures of from 50 to 140° C. and at atmospheric pressure or under autogeneous pressure.

Initiators which can be used for the free-radical polymerization are the water-soluble and water-insoluble peroxo and/or azo compounds customary for this purpose, for example alkai metal or ammonium peroxydisulfates, dibenzoyl peroxide, tert-butyl perpivalate, tert-butyl per-2-ethylhexanoate, di-tert-butyl peroxide, tert-butyl hydroperoxide, azobisisobutyronitrile, azobis(2-amidinopropane) dihydrochloride or 2,2'-azobis(2-methyl-butyronitrile). Also suitable are initiator mixtures or redox initiator systems such as ascorbic acid/iron(II) sulfate/sodium peroxodisulfate, tert-butyl hydroperoxide/sodium sulfite, tert-butyl hydroperoxide/sodium hydroxymethane-sulfinate. The initiators can be used in the customary amounts, for example in amounts of from 0.05 to 5% by weight, based on the amount of monomers to be polymerized.

The cosmetic preparations preferably comprise from 0.2 to 20% by weight of the polymer.

The invention further relates to a process for the preparation of the above-described polymers, in which, following the polymerization, which is preferably carried out as a solution polymerization, the resulting polymer is treated directly with hydrogen peroxide and/or activated carbon and/or a volatile vegetable oil (essential oil) at a temperature between 70 and 120° C.

Hydrogen peroxide is used here in an amount up to 1% by weight, activated carbon up to 5% by weight and the essential oil up to 1% by weight, in each case based on the polymer solution.

Suitable essential oils are, for example, lavender oil, rose oil, cinnamon oil, almond oil and coconut oil.

This process achieved an improvement in the odor and also the color of the polymer.

The polymers in the cosmetic preparations are preferably either partially or completely neutralized using a monohydric acid or a polyhydric acid or a polycarboxylic acid, or are quaternized in a customary manner using a quaternizing agent (alkyl halide or dialkyl sulfate).

In particular, the polymer is partially or completely neutralized using phosphoric acid or an acid mixture containing phosphoric acid.

Acids which can be used are organic acids, mono-, di-, tricarboxylic acids (e.g. fatty acid, lactic acid, tartaric acid, citric acid) or mineral acids (e.g. hydrochloric acid, $H_2SO_4$, $H_3PO_4$).

In order to keep the residual vinyllactam(VP or VCap) content low, the product solutuion, following polymerization, is afterpolymerized using 2,5-dimethyl-2,5-di(tert-butylperoxy)-hexane,(Trigonox 101) at about 130° C./3–10 h. This lowers the residual content of vinyllactam monomers to <100 ppm.

The invention also relates to the use of the novel polymers for cosmetic preparations, in particular as setting polymers in hair spray, foam setting compositions, hair mousse, hair gel and shampoos.

Other suitable fields of use are cosmetic skin preparations and nail varnishes.

The novel polymers preferably have a glass transition temperature above 250° C. and a K value of from 25 to 70, preferably from 25 to 50 (measured in accordance with Fikentscher).

The invention further relates to cosmetic hair preparations comprising
(a) from 0.2 to 20% by weight of a polymer as claimed in one of claims 1 to 6,
(b) from 0 to 10% by weight of a conventional hair-setting polymer,
(c) from 0 to 1% by weight of a water-dispersible siloxane-containing compound,
(d) from 30 to 99.5% by weight of a solvent or solvent mixture of alcohol, in particular ethanol, and water,
(e) from 0 to 60% by weight of a propellant of dimethyl ether and/or propane/butane,
(f) from 0 to 0.3% by weight of a cosmetically suitable additive.

It is also possible to mix the polymers to be used according to the invention with conventional hair cosmetics polymers if the intention is to achieve particular properties. Examples of conventional hair cosmetics polymers are
  cationic (quaternized) polymers, e.g. cationic polyacrylate copolymers based on N-vinyllactams and derivatives thereof (N-vinylpyrrolidone, N-vinylcaprolactam etc.) and customary catonic hair-conditioning polymers, e.g. Luviquat® (copolymer of vinylpyrrolidone and vinylimidazolium methochloride), Luviquat® Hold (copolymer of quaternized N-vinylimidazole, N-vinylpyrrolidone and N-vinylcaprolactam), Merquat® (polymer based on dimethyldiallylammonium chloride), Gafquat® (quaternary polymers produced by reacting polyvinylpyrrolidone with quaternary ammonium compounds), polymer JR (hydroxyethylcellulose containing cationic groups), polyquaternium products (CTFA names), etc.;

nonionic, water-soluble or water-dispersible polymers or oligomers, such as polyvinylcaprolactam, e.g. Luviskol Plus (BASF), or polyvinylpyrrolidone and copolymers thereof, in particular with vinyl esters, such as vinyl acetate, e.g. Luviskol VA 37 (BASF); polyamides, e.g. those based on itaconic acid and aliphatic diamines;

amphoteric or zwitterionic polymers such as the octylacrylamide-methyl methacrylate—tert-butylaminoethyl methacrylate—2-hydroxypropyl methacrylate copolymers, obtainable under the names Amphomor® (Delft National), and zwitterionic polymers, as disclosed, for example, in German Patent Applications DE 39 29 973, DE 21 50 557, DE 28 17 369 and DE 37 08 451. Acrylamidopropyltrimethylammonium chloride—acrylic acid or—methacylic acid copolymers and alkali metal and ammonium salts thereof are preferred zwitterionic polymers. Other suitable zwitterionic polymers are methacroylethylbetain—methacrylate copolymers, which are obtainable commercially under the name Amersette® (AMERCHOL);

nonionic, siloxane-containing, water-soluble or dispersible polymers, e.g. polyethersiloxanes, such as Tegopren® (Goldschmidt) or Belsil® (Wacker).

The polymers to be used according to the invention are generally suitable as hair-setting polymers having a conditioning action in cosmetic preparations, especially in cosmetic hair preparations such as hair treatments, hair lotions, hair rinses, hair emulsions, fluids for treating hair ends, neutralizing agents for permanent waves, "hot-oil treatment" preparations, conditioners, shampoos, setting lotions or hair sprays.

Depending on the field of use, the cosmetic hair preparations can be applied as a spray, foam, gel, gel spray or mousse. Preference is given to the use as a hair spray.

As well as containing the novel polymers and suitable solvents such as water or water/alcohol mixtures, the cosmetic hair preparations can also contain additives which are customary in cosmetics, such as emulsifiers, preservatives, perfume oils, care substances such as panthenol, collagen, vitamins, protein hydrolysates, stabilizers, pH regulators, dyes and other customary additives.

A particularly suitable additive for the polymers according to the invention are fatty acid amides, in particular those with a chain length of $C_{12}$–$C_{22}$. Particular preference is given to erucamide and stearamide. The fatty acid amides are used in an amount of up to 0.1% by weight, based on the polymer.

The polymers according to the invention can also be used in cosmetic preparations for protecting and caring for the skin, for example as moisturizing cream or lotion.

General Preparation Procedure (Solution Polymerization)

EXAMPLE 1

Feed 1: 1200 g of a monomer mixture of 612 g of tert-butyl acrylate, 120 g of dimethylaminopropylacrylamide and 468 g of vinylpyrrolidone Feed 2: 2.4 g of Wako V59=2,2'-azobis(2-methylbutyronitrile) in 450 g of ethanol Feed 3: 3.6 g of Wako V59 in 90 g of ethanol Feed 4: 77 g of 40% strength (in ethanol) phosphoric acid A mixture of 240 g of Feed 1, 60 g of Feed 2 and 270 g of ethanol was heated to 75° C. After polymerization had started, recognizable from an increase in viscosity, the remainder of Feed 1 was added over 4 h and Feed 2 was added over 5 h at 78° C. with stirring, and the mixture was polymerized for a further 4 h at 80° C. After Feed 3 has been metered in over ½ h, the product was after-polymerized for 8 h at 80° C. At a temperature of about 40° C., Feed 4 was metered in with stirring over about 30 min to give a clear pale yellow solution.

The other products in the table below can be prepared by a similar method. The polymers have a K value (measured in 1% strength ethanolic solution) of from 37 to about 45 and a propane/butane compatibility of >60%.

The table below gives the values for the composition (% by weight), curl retention, setting, "flaking" and film properties (tack, wash-off and feel).

EXAMPLES

|   | TBA | TMBA | NtBAM | SMA | DMAPMA | VP | VCap | Curl*) Retention [%] | Setting | Flaking*) | Film*) Tack/wash-off/feel |
|---|---|---|---|---|---|---|---|---|---|---|---|
| 1 | 51 | — | — | — | 10 | 39 | — | 75 | 2 | 2 | 2/2/1–2 |
| 2 | 55 | — | — | — | 15 | 30 | — | 79 | 1–2 | 1–2 | 1–2/1–2/1–2 |
| 3 | 40 | 15 | — | — | 16 | 29 | — | 83 | 1–2 | 2 | 1–2/2/2 |
| 4 | 40 | — | 15 | — | 16 | 29 | — | 87 | 1–2 | 2 | 1–2/2/1–2 |
| 5 | 45 | — | — | 10 | 16 | 29 | — | 83 | 1–2 | 1 | 2/2/1 |
| 6 | 55 | — | — | — | 17 | 28 | — | 87 | 1–2 | 1 | 1–2/1–2/1 |
| 7 | 59 | — | — | — | 23 | 18 | — | 71 | 1–2 | 1–2 | 2/1/1–2 |
| 8 | 63 | — | — | — | 30 | 7 | — | 76 | 2 | 2 | 2–3/1/1–2 |
| 9 | 60 | — | — | — | 30 | — | 10 | 80 | 1–2 | 2 | 1–2/1–2/1–2 |

-continued

| | TBA | TMBA | NtBAM | SMA | DMAPMA | VP | VCap | Curl*) Retention [%] | Setting) | Flaking*) | Film*) Tack./ wash-off/feel |
|---|---|---|---|---|---|---|---|---|---|---|---|
| 10 | 35 | — | — | 20 | 15 | 30 | — | 67 | 2 | 1–2 | 2/1/2 |
| 11 | 25 | — | — | 30 | 15 | 30 | — | 60 | 2–3 | 1 | 2–3/1/1–2 |
| 12 | — | — | 25 | 30 | 15 | 30 | — | 77 | 1–2 | 1 | 1–2/1/2 |
| 13 | — | — | 15 | 35 | 15 | — | 30 | 75 | 1–2 | 1–2 | 1–2/1/1–2 |

*)Curl retention, setting, flaking and film were determined from the VOC 95 aerosol hair spray formulation (containing 50 parts of propane/butane)
TBA: tert.-butyl acrylate
TMBA: tert-butyl methacrylate
NtBAM: tert-butylacrylamide
SMA: Stearin methacrylate
VP: vinylpyrrolidone
VCap: vinylcaprolactam
DMAPMA: dimethylaminopropylmethacrylamide Curl retention is a measure of the hair-setting action under extreme climatic conditions. It is measured in a dummy experiment on hair curls which have been produced using a customary permanent wave on hair about 15 cm in length and sprayed with the spray preparation in question from a distance of 10 cm for 4 sec. After the curls have been hung up in a climatically controlled chamber at 25° C. and 90% relative atmospheric humidity for a period of 5 h, the relative deformation (extension) of the curls, based on their original shape, is determined. A high value indicates a high setting action, i.e. at 100%, the original shape is completely retained.

The setting test (the setting strength of a polymer on the hair of a dummy head), flaking (residual polymer on the hair after brushing), tack, ability of the polymer to be washed out of the hair and the feel of the treated hair are each assessed on a scale of 1 to 4 by experts:

1=very good
2=good
3=still acceptable
4=poor

Application Examples

| Aerosol hair sprays: | | |
|---|---|---|
| VOC 95 = | Polymer No. 1 to 9 | 5 parts |
| | Ethanol | 55 parts |
| | Propane/butane | 40 parts |
| | Additive: silicone, perfume | |
| VOC 95 = | Polymer No. 1 to 9 | 5 parts |
| | Ethanol | 45 parts |
| | Propane/butane | 50 parts |
| | Additive: silicone, perfume | |
| VOC 80 = | Polymer No. 1 to 9 | 5 parts |
| | Water | 15 parts |
| | Ethanol | 40 parts |
| | DME | 40 parts |
| | Additive: silicone, perfume | |
| VOC 55 = | Polymer No. 1 to 9 | 3 parts |
| | Water | 42 parts |
| | Ethanol | 15 parts |
| | DME | 40 parts |
| | Additive: silicone, perfume | |
| Pumpsprays: | | |
| VOC 95 = | Polymer No. 1 to 9 | 5 parts |
| | Ethanol | 95 parts |
| | Additive: silicone, perfume | |

-continued

| VOC 80 = | Polymer No. 1 to 9 | 5 parts |
|---|---|---|
| | Water | 15 parts |
| | Ethanol | 80 parts |
| | Additive: silicone, perfume | |
| Polymer 1 to 13 (25% strength aqueous solution) | | 20.0 |
| Cremophor A 25 (Ceteareth 25/BASF) | | 0.2 |
| Comperlan KD (Cocamide DEA/Henkel) | | 0.1 |
| Water | | 69.7 |
| Propane/butane | | 10.0 |
| Erucamide | | 0.0005 |
| Other additives: perfume, preservatives . . . | | |

Preparation: Weigh out and dissolve with stirring. Draw off into containers and add propellant.

| | Conditioner Shampoo | [%] |
|---|---|---|
| A) | Texapon NSO 28% strength (Sodium Laureth Sulphate/Henkel) | 50.0 |
| | Comperlan KD (Cocamide DEA/Henkel) | 1.0 |
| | Polymer 1 to 13 (25% strength aqueous solution) | 20.0 |
| | Erucamide | 0.001 |
| | q.s. perfume oil | |
| B) | Water | 27.5 |
| | Sodium chloride | 1.5 |
| | q.s. preservative . . . | |

Preparation: Weigh out and, with stirring, separately dissolve and mix phases A and B. Slowly stir phase B into phase A.

| Standard O/W cream | | |
|---|---|---|
| Oil phase | [%] | CTFA name |
| Cremophor A6 | 3.5 | Ceteareth-6 (and) Sterayl Alcohol |
| Cremophor A25 | 3.5 | Ceteareth-25 |
| Glycerol monostearate s.e. | 2.5 | Glyceryl Stearate |
| Paraffin oil | 7.5 | Paraffin Oil |
| Cetyl alcohol | 2.5 | Cetyl Alcohol |
| Luvitol EHO | 3.2 | Cetearyl Octanoate |
| Vitamin E acetate | 1.0 | Tocopheryl Acetate |

-continued

| Standard O/W cream | | |
|---|---|---|
| Stearamide | 0.001 | |
| Nip-Nip | 0.1 | Methyl- and Propyl-4-hydroxy-benzoate (7:3) |

| Water phase | [%] | |
|---|---|---|
| Polymer 1 to 13 | 1.5 | |
| Water | 73.6 | Water |
| 1,2-Propylene glycol | 1.0 | Propylene Glycol |
| Germall II | 0.1 | Imidazolidinyl-urea |

Preparation: Weigh out and, with stirring, separately homogenize the oil phase and the water phase at a temperature of about 80° C. Slowly stir the water phase into the oil phase. Slowly cool to RT with stirring.

| O/W lotion | | |
|---|---|---|
| Oil phase | [%] | CTFA name |
| Cremophor A6 | 2.0 | Ceteareth-6 (and) Stearyl Alcohol |
| Cremophor A25 | 2.0 | Ceteareth-25 |
| Glycerol monostearate | 6.0 | Glyceryl Stearate |
| Paraffin oil | 0.9 | Paraffin Oil |
| Tegiloxan 100 | 0.1 | Dimethicone |
| Cetyl alcohol | 1.5 | Cetyl Alcohol |
| Luvitol EHO | 12.0 | Cetearyl Octanoate |
| Vitamin E acetate | 0.4 | Tocopheryl Acetate |
| Erucamide | 0.001 | |
| Nip-Nip | 0.1 | Methyl- and Propyl-4-hydroxy-benzoate (7:3) |

| Water phase | [%] | |
|---|---|---|
| Polymer 1 to 13 | 1.0 | |
| Water | 73.4 | Water |
| 1,2-Propylene glycol | 1.0 | Propylene Glycol |
| Germall II | 0.1 | Imidazolidinyl-Urea |

Preparation: weigh out and, with stirring, separately homogenize the oil phase and water phase at a temperature of about 80° C. Slowly stir the water phase into the oil phase. Slowly cool to RT with stirring.

Example 14 (TBA:DMAPMA:VP:SMA:Belsil= 50.5:15:28:6:0.5)

(1) 2.4 g of Belsil® DMC 6031 (Wacker), 6 g of water and 64 g of ethanol were introduced into the polymerization reactor which had been flushed beforehand with $N_2$.
(2) The solution was heated to 75° C. and stirred.
(3) 242.4 g of TBA, 72 g of DMAPMA, 134.3 g of VP and 28.8 g of SMA were added.
(4) 1 g of 2,2'-azobis(2-methylbutyronitrile) (V-59, WAKO), dissolved in 170 g of ethanol, were added.
(5) After a temperature of 70° C. had been reached, 96 g of the monomer feed and 17 g of the initiator solution were added.
(6) The remaining monomer feed and the initiator addition were added over the course of 4 to 5 hours.
(7) After completion of the feed, the mixture was stirred for a further 2 hours at 80° C.
(8) optionally after treatment with hydrogen peroxide and activated carbon, the polymer was neutralized with lactic acid.

The following polymers (Example 15 to 22) were prepared as in Example 14.

TABLE

| Example | TBA | DMAPMA | VP | SMA | DMC 6031 |
|---|---|---|---|---|---|
| 15 | 29 | 15 | 25 | 29 | 2 |
| 16 | 36 | 16 | 28 | 18 | 2 |
| 17 | 47 | 16 | 28 | 0 | 9 |
| 18 | 54 | 16 | 28 | 0 | 2 |
| 19 | 50 | 15 | 28 | 6 | 1 |
| 20 | 56 | 15 | 28 | 0 | 1 |
| 21 | 50 | 16 | 28 | 6 | 0 |
| 22 | 50.5 | 15 | 28 | 6 | 0.5 |

We claim:

1. A cationic polymer obtained by free-radical copolymerization of components consisting of
   (a) from 50 to 70% by weight of one or more monomers of the formula I

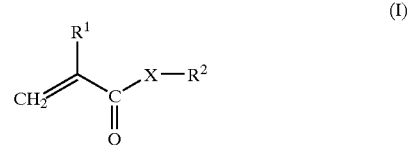

$X=O, NR^1$
   $R^1=H, C_1-C_8$-alkyl
   $R_2=$tert-butyl,
   (b) from 5 to 45% by weight of one or more monomers of formula II

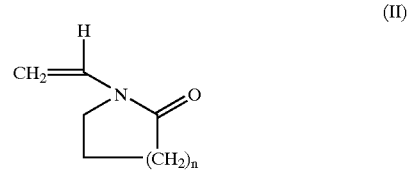

where n=1 to 3,
   (c) from 5 to 40% by weight of a monoethylenically unsaturated monomer having at least one amine-containing group where up to 40% by weight, based on (a), (b), and (c) of the monomer (a) can be replaced by a monomer of the formula I where $R^2=C_2-C_{22}$-alkyl.

2. A polymer as claimed in claim 1, obtained by free-radical copolymerization of
   (a) from 51 to 65% by weight of the monomer of the formula I,
   (b) from 7 to 39% by weight of the monomer of the formula II,
   (c) from 10 to 30% by weight of the amine-containing monomer.

3. A polymer as claimed in claim 1, wherein the monomer (a) is tert-butyl acrylate, N-tert-butylacrylamide or tert-butyl methacrylate.

4. A polymer as claimed in claim 1, wherein the monomer (b) is vinylpyrrolidone or vinylcaprolactam.

5. A polymer as claimed in claim 1, wherein the monomer (c) is dimethylaminoalkyl (meth)acrylate or dimethylaminoalkyl (meth)acrylamide.

6. A polymer as claimed in claim 1, wherein the monomers of the formula I where $R_2=C_2-C_{22}$-alkyl are N-butylacrylamide, -octylacrylamide, lauryl (meth)acrylate or stearyl(meth)acrylate.

* * * * *